(12) United States Patent
Matsutani et al.

(10) Patent No.: US 8,597,326 B2
(45) Date of Patent: Dec. 3, 2013

(54) SUTURING NEEDLE

(75) Inventors: Kanji Matsutani, Utsunomiya (JP);
Yoshimasa Tochimura, Utsunomiya (JP); Masayuki Watanabe, Utsunomiya (JP); Shinichi Akutsu, Utsunomiya (JP)

(73) Assignee: Mani, Inc., Utsunomiya-Shi (JP)

( * ) Notice: Subject to any disclaimer, the term of this patent is extended or adjusted under 35 U.S.C. 154(b) by 536 days.

(21) Appl. No.: 12/521,928

(22) PCT Filed: Dec. 27, 2007

(86) PCT No.: PCT/JP2007/075190
§ 371 (c)(1),
(2), (4) Date: Jul. 1, 2009

(87) PCT Pub. No.: WO2008/084722
PCT Pub. Date: Jul. 17, 2008

(65) Prior Publication Data
US 2010/0023054 A1 Jan. 28, 2010

(30) Foreign Application Priority Data

Jan. 11, 2007 (JP) ................................. 2007-002927
May 31, 2007 (JP) ................................. 2007-144973

(51) Int. Cl.
*A61B 17/06* (2006.01)
(52) U.S. Cl.
USPC ........................................................ 606/223

(58) Field of Classification Search
USPC .............. 606/222–224, 225–227; 112/35, 37, 112/222–227
See application file for complete search history.

(56) References Cited

U.S. PATENT DOCUMENTS 3,160,157 A * 12/1964 Chisman ....................... 606/223
5,693,072 A    12/1997 McIntosh
2006/0047309 A1 * 3/2006 Cichocki ....................... 606/222

FOREIGN PATENT DOCUMENTS

JP        43-015511 B1   6/1968
JP        07-178101 A    7/1996

* cited by examiner

*Primary Examiner* — Melanie Tyson
*Assistant Examiner* — Son Dang
(74) *Attorney, Agent, or Firm* — Smith Patent Office

(57) ABSTRACT

A suturing needle, comprising needle tip portion (1) having needle tip (1a), tapered portion (2) continuing to needle tip portion (1), trunk portion (3) continuing to tapered portion (2), and thread attaching portion (4) continuing to trunk portion (3); needle tip portion (1) has circular section continuing to sharp needle tip (1a), angular section continuing to sharp needle tip (1a), circular section continuing to blunt needle tip (1a) or angular section continuing to blunt needle tip (1a): wherein trunk portion (3) has the relations R1≥R2≥R3, when peak (5) or joint portion between the two flat faces has diameter R1, crest of ridges has a roundness of R2, and a valley (7) has roundness R3; and valley (7) is formed to correspond partially to peak (5), and the thickness becomes continuously larger from tapered portion (2) to trunk portion (3).

11 Claims, 7 Drawing Sheets

SUTURING NEEDLE

TECHNICAL FIELD

The present invention relates to a suturing needle having a sharp needle tip or a blunt needle tip. More specifically, the present invention relates to a suturing needle which can be reliably held by a needle holder for action of a high thrust.

BACKGROUND ART

Suturing needles used for suturing the biological tissues are broadly divided into a form of piercing the tissues to be sutured and extending by force and passing through the tissues and a form of cutting and passing through the pierced tissues as a base point. The suturing needle optimum for the tissues to be sutured is selected for use.

The suturing needle having the former form is formed as a circular needle having a circular section in its entirety from a needle tip portion for piercing the tissues through a trunk portion to a distal end. A needle tip as the tip of the needle tip portion is formed to have a sharp point or a blunt spherical shape. The suturing needle having the latter form is formed as an angular needle having a section from a needle tip to a trunk portion, which has a polygonal shape represented by a triangular shape. A needle tip is formed to have a sharp point or a blunt shape concentrated by plural faces configuring the polygonal shape. Cutting edges are formed on two or more ridge lines configuring the angular shape.

To realize easy suturing by reducing the labor of an operator, the circular needle and the angular needle have been improved in view of how much the resistance (piercing resistance) is reduced when piercing and passing through the biological tissues. However, even if the piercing resistance is reduced, the entire resistance cannot be eliminated.

Being too sharp in order to reduce the piercing resistance, the tip easily pierces the glove or skin of the operator to damage his/her skin. Infection due to the blood or body fluid of a patient can occur.

In order not to easily tear the glove on contact with the tip, the circular needle having the blunt tip has been proposed (see U.S. Pat. No. 5,693,072). In this technique, a needle tip portion (a tip portion 12) is formed to have a circular section and a spherical tip. To exhibit good stability and operability in use, a trunk portion (a shaft portion 11) has an hourglass-like or rectangular section having two flat faces.

For the angular needle, there has been proposed the suturing needle which has the blunt tip by grinding one face configuring a polygonal shape (see Japanese Patent Application Laid-Open (JP-A) No. 6-296790). In this technique, even if the blunt needle tip is brought into contact with the operator, the risk of hurting him/her is reduced. The risk of infection due to the blood or body fluid of the patient can be reduced.

The suturing needle is held by a needle holder for operation. The curved suturing needle held by the needle holder can be rotated by the acting force in the operation by the needle holder. Thus, there has been proposed a technique in which at least one plane region is formed in the longitudinal direction of the suturing needle and at least one rib or, if possible, two ribs in the longitudinal direction are formed in the plane region so as to engage the sawtooth portions of the needle holder, thereby preventing the rotation of the suturing needle (see Japanese Patent Application Publication (JP-B) No. 43-15511).

DISCLOSURE OF THE INVENTION

The entire piercing resistance of the suturing needle, such as the circular needle and the angular needle, for piercing the biological tissues acts on the needle holder. It is, therefore, essential to reliably hold the suturing needle by the needle holder. The operator needs to reliably hold the suturing needle by the needle holder. In the technique of JP-B No. 43-15511, a sufficient function for preventing the suturing needle held by the needle holder from being rotated can be exhibited. However, according to the position of the rib(s) formed in the plane region, the suturing needle is rotated when being originally held by the needle holder and the transmission of a high thrust to the suturing needle is not sufficient.

When the needle tip is blunt in order not to pierce the glove or skin of the operator, a force stronger than the reduced piercing resistance of the suturing needle which has been typically used is necessary when the suturing needle pierces the biological tissues. The curved suturing needle can be deformed so as to open the curved shape by the force.

An object of the present invention is to provide a suturing needle, which can be reliably held by a needle holder, which can transmit a high thrust, and which can reduce the risk of damaging an operator, and the deformation when a strong force acts.

To address the above problems, the present inventors have conducted some experiments of the holding of the suturing needle by the needle holder. As a result, it has been found that when the angles of R2 and R3 are set to be smaller than the angles of the convex and concave portions of the holding face of the needle holder, the holdability is good. This will be described with R3 (the roundness of the valley). The convex portion of the holding face of the needle holder enters into the valley (R3). The difference in angle between the convex portion of the holding face of the needle holder and the valley is large. The convex portion is assumed to be easily brought into contact with the upper and large area of the face configuring the valley.

R of the convex portion of the holding face of the needle holder is smaller and sharper than R3. If the angles of R3 and the convex portion are the same, the convex portion makes a point contact with the bottom portion of R3. The holdability becomes poor. For the suturing needle manufacturing method, the roundness of the valley cannot be eliminated so that the angle of the convex portion is smaller. R2 (the roundness of the crest) is equal to or larger than R3. R2 does not deeply enter into the concave portion of the holding face of the needle holder. The convex portion can relatively deeply enter into R3 and is brought into contact with the large area of R3. The holdability becomes good. R1 (the radius of the peak as the joint portion between the flat faces) is equal to or larger than R3. The convex portion can easily enter into R3.

R1 acts as the peak of the suturing needle. When an austenitic stainless steel wire is cold-drawn as a raw material, the larger R of the peak is excellent in ductility. R1 is preferably set to the largest R. The radius R1 of the peak is preferably set to the largest roundness.

A suturing needle according to the present invention includes: a needle tip portion having a needle tip for piercing the tissues, a tapered portion continuing to the needle tip portion, a trunk portion continuing to the tapered portion, and a thread attaching portion continuing to the trunk portion for connecting the suturing thread. The suturing needle is characterized in that the needle tip portion is formed to have a circular section continuing to the sharp needle tip, an angular section continuing to the sharp needle tip, a circular section continuing to the blunt needle tip or an angular section continuing to the blunt needle tip, in that the tapered portion is formed to become gradually thicker from the needle tip portion to the trunk portion, in that the trunk portion is formed to have a substantially triangular section, the upper face of which is formed of a wave shape having at least two ridges and the slopes of which are formed of two flat faces, in that the trunk portion is also formed to have relations of $R1 \geq R2 \geq R3$, when a peak or the joint portion between the two flat faces has a radius of $R1$, the crest of the ridges has a roundness of $R2$, and a valley has a roundness of $R3$, in that the valley is formed to correspond partially to the peak, and in that the thickness becomes continuously larger from the tapered portion to the trunk portion.

Also, a suturing needle according to the present invention is a curved suturing needle having a needle tip portion having a needle tip for piercing the tissues, a trunk portion continuing to the needle tip portion, and a distal end having a function of connecting the suturing thread and continuing to the trunk portion, wherein the needle tip is formed to be rounded or flat blunt, the trunk portion is formed to have a substantially triangular section having a curved peak and a face opposite the peak, the trunk portion is formed so that the peak is arranged on the outer circumferential side of a curve and the face is arranged on the inner circumferential side of the curve, and the trunk portion is formed so that at least two ribs (ridges) are provided in the longitudinal direction of the suturing needle on the face opposite the curved peak to form a groove (valley) between the two adjacent ribs (ridges) and that one extension line of a vertical line of the groove (valley) relative to the face crosses a portion of the peak.

The "roundness of the crest of the ridges" and the "roundness of the valley" referred in the present invention are respectively referred to as the "ridge" and the "valley" configuring the "wave shape" continuously formed on the upper face. R formed so that the wave shape is discontinued at the end of the upper face is not included in the "roundness of the crest of the ridges" and the "roundness of the valley" referred in the present invention.

The suturing needle according to the present invention is characterized in that the trunk portion is formed to have a substantially triangular section, the upper face of which is formed of a wave shape having at least two ridges and the slopes of which are formed of two flat faces, in that the trunk portion is also formed to have relations of $R1 \geq R2 \geq R3$, when a peak or the joint portion between the two flat faces has a radius of $R1$, the crest of the ridges has a roundness of $R2$, and a valley has a roundness of $R3$, and in that the valley is formed to correspond partially to the peak. The suturing needle engages the sawtooth convex and concave portions formed onto the holding face of the needle holder to realize reliable holding. The suturing needle can be strongly held to reliably transmit a thrust and cannot be rotated by the acting force for suturing.

The thickness becomes continuously larger from the tapered portion to the trunk portion. No large resistance can be caused when the suturing needle pierces the biological tissues.

The needle tip is formed to be rounded or flat blunt. The suturing needle cannot damage the glove or skin of the operator. A force applied when the blunt needle tip pierces the tissues acts in the direction of opening the curve. However, the trunk portion has a triangular section in which the peak is arranged on the outer circumferential side of the curve and the face is arranged on the inner circumferential side of the curve. Thus, the limited sectional area can be effectively used to exhibit high resistance relative to the acting bending force, thereby reducing deformation.

EXPLANATION OF REFERENCE NUMERALS

A Suturing needle
1 Needle tip portion
1a Needle tip
2 Tapered portion
3 Trunk portion
4 Thread attaching portion
5 Peak
6 Ridge
7 Valley
10 Lower mold
10a Slope
11 Upper mold
11a Molding face
15 Raw material
16 Intermediate member
21 Needle tip
22 Needle tip portion
22a Needle tip
23 Tapered portion
24 Trunk portion
30 Needle holder
31 Bar

BEST MODE FOR CARRYING OUT THE INVENTION

The most preferred embodiment of a suturing needle of the present invention will be described below. The suturing needle of the present invention can be reliably held by a needle holder, can prevent the shift and rotation relative to the needle holder during a suturing operation for the biological tissues, and can transmit a high thrust.

The suturing needle of the present invention has a needle tip portion including a needle tip, a tapered portion continuing to the needle tip portion, a trunk portion continuing to the tapered portion, and a thread attaching portion continuing to the trunk portion. Either of a straight suturing needle and a curved suturing needle of the present invention is preferably applicable.

Either of a sharp needle tip and a blunt needle tip is applicable. The needle tip portion is formed to have a circular section or an angular section continuing to the sharp or blunt needle tip. In the angular section, cutting edges are preferably formed at least at two edges.

Plural thicknesses and outer shapes of the suturing needle are standardized in JIS or ISO. The thickness of the trunk portion is set within the range of 0.025 to 1.40 mm, for example.

According to the present invention, the material configuring the suturing needle is not limited. A steel wire, a martensitic stainless steel, and an austenitic stainless steel can be selectively used. In the case of the steel wire and the martensitic stainless steel, hardening by thermal treatment can be expected and it is difficult to prevent the generation of rust. In the case of the austenitic stainless steel, hardening by thermal treatment cannot be expected and rust cannot be caused. Considering rust, the austenitic stainless steel is preferably used.

The austenitic stainless steel wire is cold-drawn by a predetermined reduction of area to realize a high hardness. The material made by extending an austenitic tissue into fibers to improve the strength relative to bending is used. Preferably, the material can improve the piercing properties to the biological tissues and can resist the acting bending force during the suturing operation.

The trunk portion of the suturing needle of the present invention is formed to have a substantially isosceles triangular shape having an upper face and two faces as lower slopes. The upper face is formed in a wave shape having at least two ridges. A valley formed between the ridges is formed to correspond partially to the joint portion between the two faces as lower slopes. The trunk portion is also formed to have relations of $R1 \geq R2 \geq R3$, when the joint portion (hereinafter, referred to as a "peak") between the two flat slopes has a radius of R1, the crest of the ridges has a roundness of R2, and a valley has a roundness of R3.

The dimensions of R1 to R3 are applicable to the sawtooth convex and concave portions formed in the currently available needle holder and are set to values so that the suturing needle can be stably held by the needle holder by a different maker. In the experiments of the present inventors, it has been evident that the suturing needle can be stably held by the needle holder by the different maker by setting the roundness of the ridges, the roundness of the valley, and the radius of the peak to the above relations.

However, the pitch of the convex and concave portions of the needle holder is not always constant and is different according to the maker. Thus, in the suturing needle of the present invention, the roundness of the ridges is set to R2 and the roundness of the valley is set to R3, but the pitch of the ridge is not uniquely set and preferably corresponds to the pitch of the needle holder.

In the suturing needle of the present invention, the portion from the tapered portion to the trunk portion is formed as a continuously thickened smooth line. The portion from the tapered portion to the trunk portion is formed by the smoothly continued line, which can reduce the piercing resistance.

In the related art suturing needle manufacturing method, when molding for forming a groove in the trunk portion is performed, the mold has a length substantially equal to the length of the groove to be formed. The portion corresponding to the tapered portion and the portion corresponding to the thread attaching portion are projected from the mold at molding. In the projected portion (in particular, the portion from the tapered portion to the trunk portion), a step is formed between the projected portion and the portion corresponding to the mold. The step becomes the piercing resistance.

In the suturing needle of the present invention, the portion from the tapered portion to the trunk portion is formed by the continuous smooth line to eliminate the step. The reduction of the piercing resistance is realized.

Embodiment 1

An embodiment of a suturing needle of the present invention will be described below with reference to the drawings.

Figure 1:
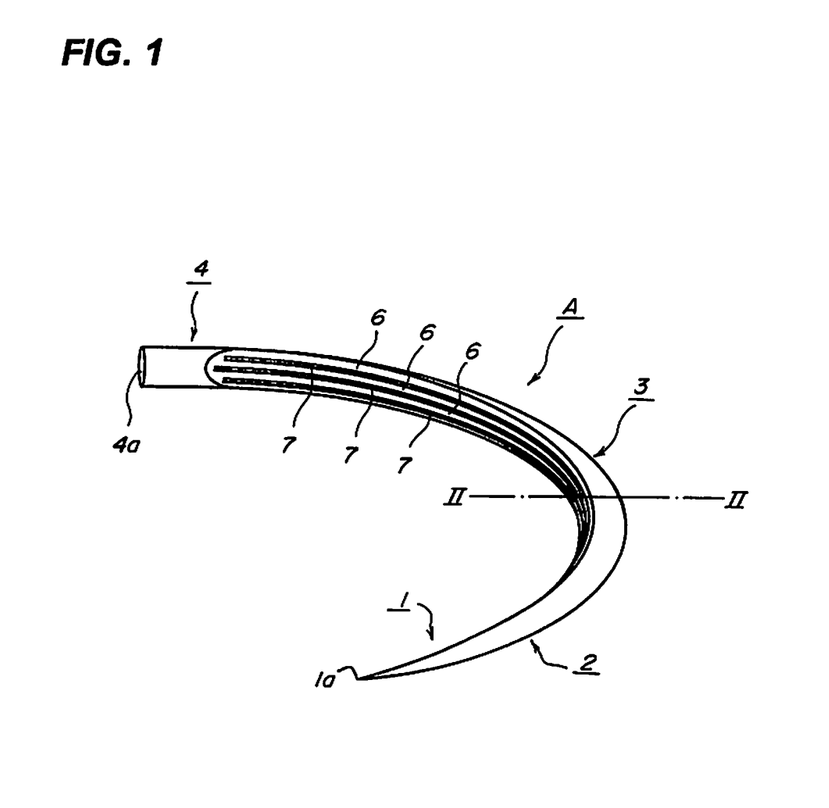
FIG. 1 is a perspective view of a suturing needle.
Figure 2:
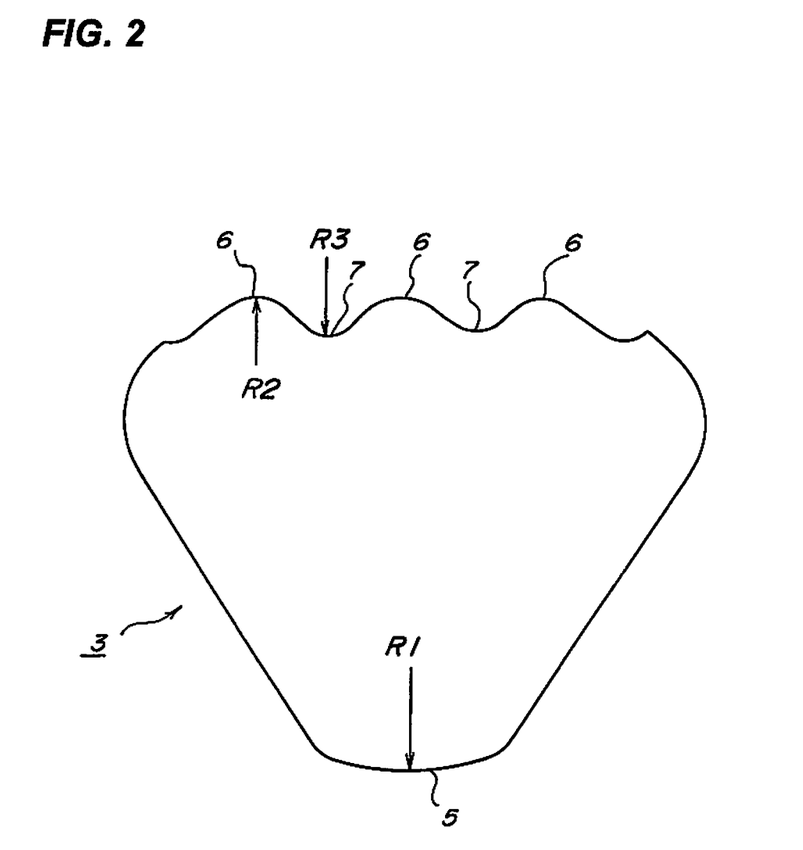
FIG. 2 is a diagram of assistance in explaining the sectional shape of a trunk portion of the suturing needle.
Figure 3:
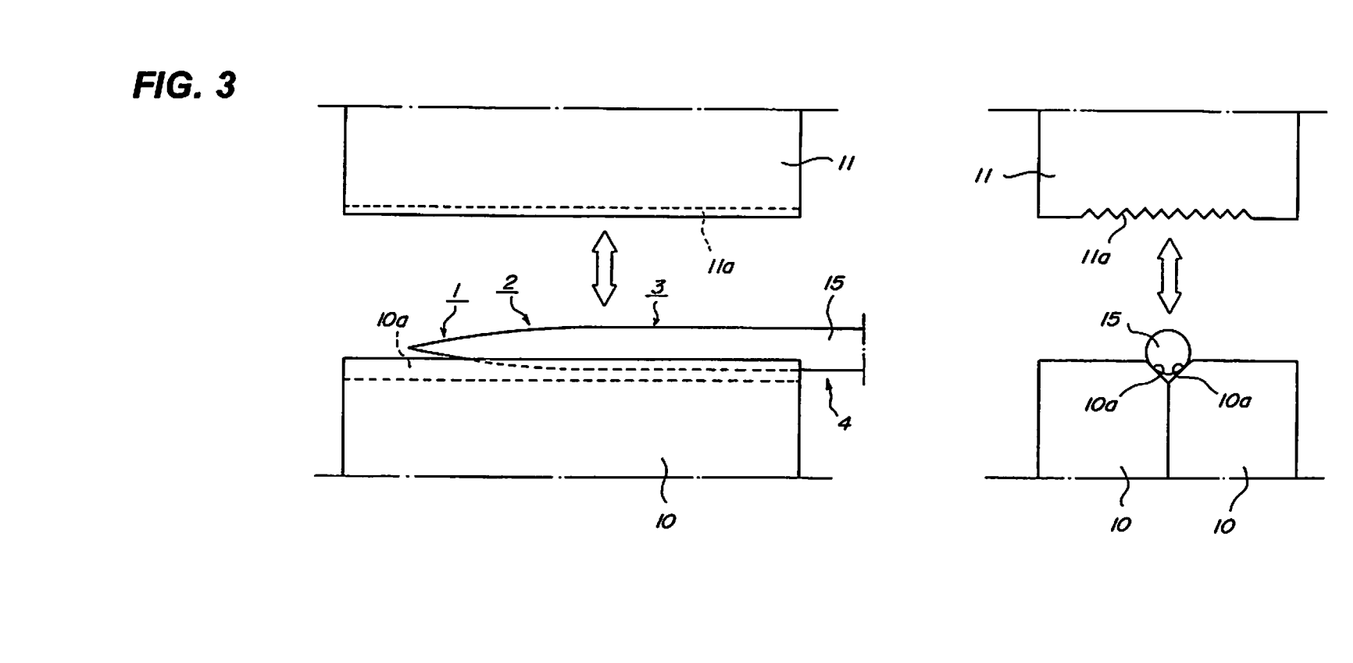
FIG. 3 is a diagram of assistance in explaining the configuration of a press mold.
Figure 4:
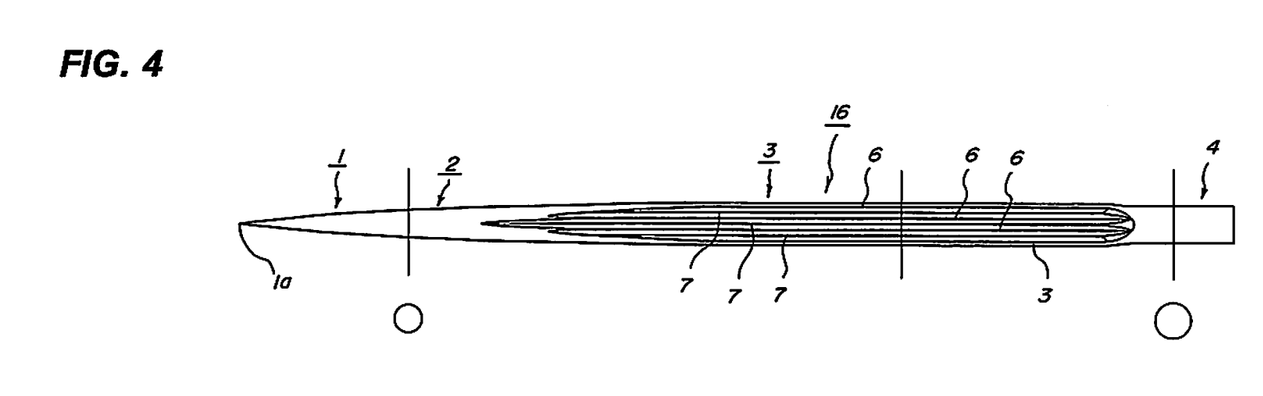
FIG. 4 is a diagram of assistance in explaining an intermediate member after pressing.

FIG. 1 is a perspective view of a curved suturing needle. FIG. 2 is a cross-sectional view of a trunk portion of the suturing needle. FIG. 3 is a diagram of assistance in explaining a mold for molding the suturing needle and a molded state. FIG. 4 is a diagram of assistance in explaining an intermediate member before the suturing needle is curved. FIGS. 5A, 5B, 5C, and 5D are diagrams of assistance in explaining examples of the shapes of a needle tip and a needle tip portion.

An illustrated suturing needle A has a needle tip portion 1, a tapered portion 2 continuing to the needle tip portion 1, a trunk portion 3 continuing to the tapered portion 2, and a thread attaching portion 4 continuing to the trunk portion 3. The suturing needle A is a curved needle formed so that the entire suturing needle is curved from the needle tip portion 1 to the thread attaching portion 4. Plural curved shapes and thicknesses of the suturing needle A are standardized. The curved shape and thickness of the optimum standard corresponding to a portion to be sutured are selected.

In the suturing needle A of this embodiment, a high hardness can be realized by cold-drawing the austenitic stainless steel wire by the predetermined reduction of area, and the material made by extending the austenitic tissue into fibers to improve the strength relative to bending is used.

The needle tip portion 1 is formed to have a circular section. The tapered portion 2 is formed to continue to the needle tip portion 1. The tapered portion 2 is formed in a tapered shape which becomes gradually thicker from the needle tip portion 1 to the trunk portion 3. The length obtained by adding the needle tip portion 1 and the tapered portion 2 is about 12 times larger than the diameter of the trunk portion 3 and is increased as the trunk portion 3 becomes thicker.

A needle tip 1a as the tip of the needle tip portion 1 is formed as a sharp tip and easily pierces the biological tissues during the suturing operation to reduce the piercing resistance. In the suturing needle A of this embodiment, the shapes of the needle tip portion 1 and the needle tip 1a are not limited to those illustrated in FIG. 1. As illustrated in FIGS. 5A, 5B, 5C, and 5D, the needle tip portion 1 and the needle tip 1a are applicable to various shapes.

Figure 5A:
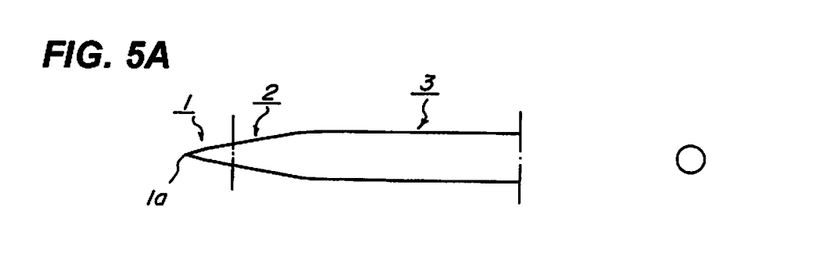
FIGS. 5A, 5B, 5C, and 5D are diagrams of assistance in explaining examples of the shapes of a needle tip and a needle tip portion.
Figures 5B, 5C:
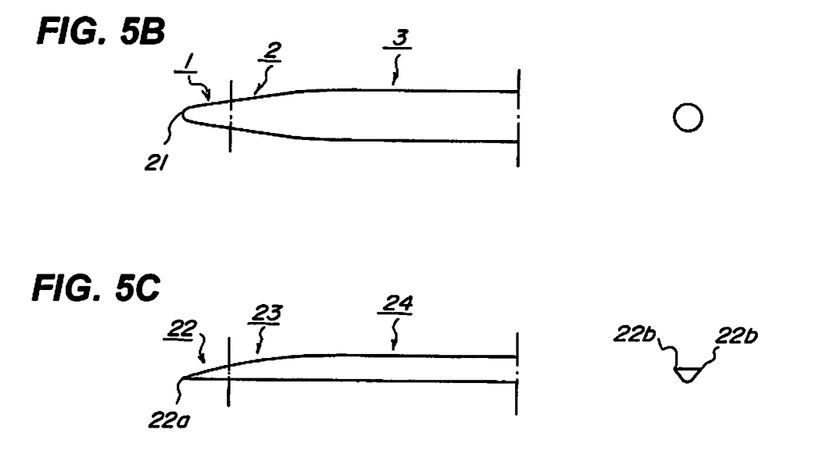

FIGS. 5A to 5D are diagrams of assistance in explaining examples of the shapes of the needle tip and the sectional shapes of the alternate long and two short dashes line portions of the needle tip portion. In FIG. 5A, the needle tip 1a illustrated in Embodiment 1 is formed to have a sharp tip and the needle tip portion 1 is formed to have a circular section. In FIG. 5B, a needle tip 21 is formed to have a spherical shape and the needle tip portion 1 is formed to have a circular section.

The diameter of the spherical shape formed in the needle tip 21 is not limited. As the diameter becomes larger, the piercing resistance when the needle tip 21 pierces the biological tissues is increased. As the diameter becomes smaller, the piercing resistance is decreased. To reduce the risk of infection due to the needle tip piercing through the glove for the operation, the risk of piercing the glove and the piercing resistance when the needle tip pierces an affected part have been required to be reduced recently. The range of the diameter of the spherical shape of the needle tip 21 satisfying such request is 0.2 to 0.6 mm and is preferably about 0.3 mm.

The shape of the needle tip 21 is not limited to the spherical shape illustrated in FIG. 5B and may be formed in a conical trapezoidal shape as a flat shape. The conical trapezoidal shape is more blunt than the spherical shape. The risk of damaging the glove or skin is reduced.

In FIG. 5C, a sharp needle tip 22a is formed at the tip of a needle tip portion 22. A tapered portion 23 is formed to continue to the needle tip portion 22. A trunk portion 24 is formed to continue to the tapered portion 23. The needle tip portion 22 is formed to have a substantially triangular section. Cutting edges 22b are formed on two ridge lines configuring the triangular shape.

Figure 5D:
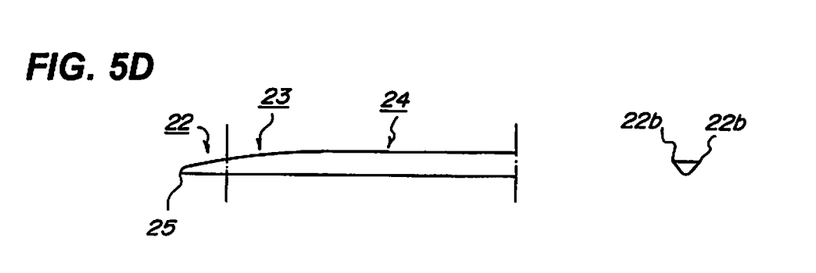

In FIG. 5D, a basic shape is the same as FIG. 5C. A blunt needle tip 25 is formed at the tip of the needle tip portion 22. The shape of the blunt needle tip 25 is not limited. The blunt needle tip 25 may be formed to have a spherical shape as in the needle tip 21 or a conical trapezoidal shape as a flat shape.

The tapered portion 2 is formed between the needle tip portion 1 and the trunk portion 3. The tapered portion 2 is formed to become gradually thicker from the needle tip 1a to the trunk portion 3 so as to reduce the piercing resistance to the biological tissues and to hold the strength of the suturing needle A. The portion from the tapered portion 2 to the trunk portion 3 is formed as a continuously thickened smooth line.

The trunk portion 3 is a portion held by the needle holder and is formed to have a substantially triangular section. The thickness of the trunk portion 3 is set within the range of 0.025 to 1.40 mm. The doctor selects and uses the suturing needle A having the optimum thickness according to an affected part to be sutured.

As illustrated in FIG. 2, the trunk portion 3 is formed to have a substantially triangular section, the slopes of which are formed of two flat faces. A peak 5 is formed in the joint portion between the two flat faces. At least two ridges (in this embodiment, three ridges) 6 are formed on an upper face which is opposite to the peak 5 arranged on the lower side. A valley 7 is formed between the ridges 6.

The peak 5 configuring the suturing needle A may be arranged on the inner side or the outer side of a curve. The peak 5 is arranged on the outer side of the curve shape. The needle tip 1a of the suturing needle A pierces an affected part and is then advanced so as to raise the suturing needle A. Reasonable section modulus and second moment of area relative to the direction in which the suturing needle A is deformed can be realized. The sectional area of the trunk portion 3 can be effectively used.

The conditions of the curve configuring the peak 5 in the section of the trunk portion 3 are not limited. The peak should not have a sharp edge.

In this embodiment, the radius R1 of the peak 5 formed in the joint portion between the two flat faces is set to about 0.5 mm. The angle formed by the two flat faces is set to about 60 degrees. The roundness R2 of the ridge 6 is set to about 0.08 mm. The angle formed by the slopes configuring the ridge 6 is set to about 85 degrees. Further, the roundness R3 of the valley 7 is set to about 0.07 mm. The angle formed by the slopes configuring the valley 7 is set to about 85 degrees.

The ridge 6 and the valley 7 formed onto the face (upper face) opposite the peak 5 are formed along the longitudinal direction of the suturing needle A. The pitch of the two ridges corresponds to the pitch of the sawtooth convex and concave portions of the needle holder and is set within the range of about 0.5 to 0.8 mm.

The valley 7 (any one of plural valleys 7 formed onto the upper face) is formed in the position where the extension line of the vertical line of the valley 7 relative to the upper face crosses a portion of the peak 5. The concave portion forming the valley 7 and the convex portion configuring the peak 5 are formed in the position where they are substantially opposite. The extension line of the vertical line of the valley 7 relative to the upper face is formed in the position where it crosses a portion of the peak 5 (a portion of the curve configuring the peak 5).

The concave portion of the valley 7 and the crest of the peak 5 need not coincide with each other. In the experiments of the present inventors, even if the concave portion of the valley 7 and the crest of the peak 5 are shifted within the range of about 0.2 mm in the lateral direction in cross section (the lateral direction in FIG. 2), the holdability of the needle holder cannot be deteriorated.

The position relation between the valley 7 and the peak 5 is strictly limited. The valley 7 and the peak 5 can be strongly held by the sawtooth convex and concave portions formed in the holding portion of the needle holder. The force of the operator can be efficiently transmitted to the suturing needle A.

Figure 7:
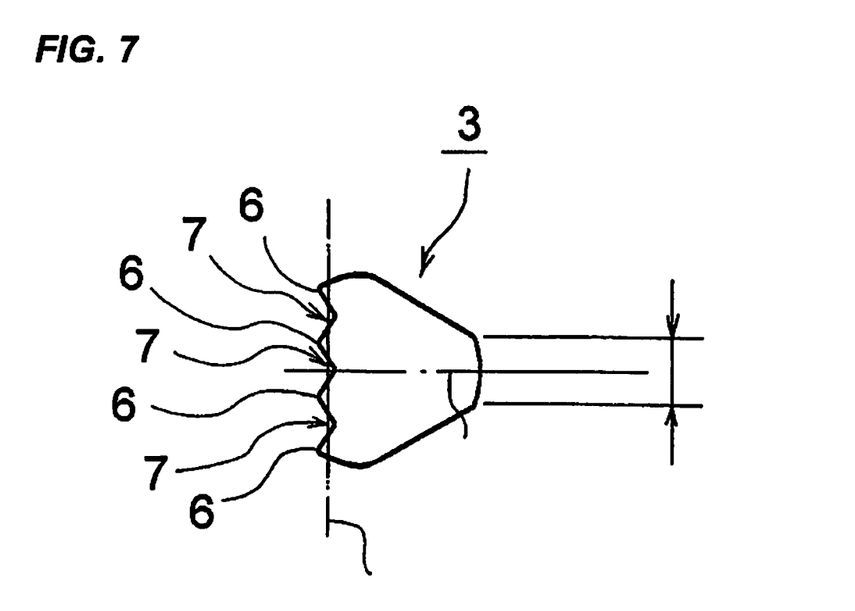
FIG. 7 is a diagram of assistance in explaining the sectional shape of the trunk portion of another suturing needle.

In the suturing needle A of this embodiment, the shape of the trunk portion 3 is not limited to that illustrated in FIG. 2. As illustrated in FIG. 7, the trunk portion 3 is applicable to various shapes. As illustrated in FIG. 7, the section of the trunk portion 3 may have a shape forming four ridges 6 and three valleys 7. The number of the ridges 6 and the valleys 7 is not limited.

The thread attaching portion 4 is a portion for attaching the suturing thread, not illustrated. There are an eyed needle having spring characteristic corresponding to the function of the suturing needle and formed with a through-hole and an eyeless needle having a distal end face formed with a blind hole. In this embodiment, the thread attaching portion 4 is formed to have a circular section and the eyeless needle formed with a hole for attaching the suturing thread to the end face is provided.

A method of Forming the Suturing Needle A

As a method of forming the suturing needle A having the above shape, there are a method of forming a triangular shape, the ridge 6, and the valley 7 by grinding a raw material having a circular section, a method of forming the peak 5, the ridge 6, and the valley 7 by pressing a raw material having a circular section, and a method of forming the peak 5 and the upper face by grinding and pressing, emitting a laser beam onto the upper face to form the valley 7 and the ridge 6. Any of these methods can be employed.

The method of processing the suturing needle A can be set in relation to the selected raw material. In the case of the material which can expect hardening by thermal treatment, it is preferred that the softened raw material be molded by pressing so as to be hardened by thermal treatment. In this case, R1 to R3 can be accurately molded by the mold. The hardened material like the cold-drawn austenitic stainless steel is preferably processed by the later-described method.

Next, the pressing method as a method of manufacturing the suturing needle A according to this embodiment will be briefly described with reference to FIGS. 3 and 4.

A press mold has a lower mold 10 and an upper mold 11 so as to be opposite and relatively separated or close. The lower mold 10 has two blocks. A slope 10a having an angle corresponding to the angle of a peak 2a in the section of the trunk portion 3 of the suturing needle A is formed in each of the blocks. The slopes 10a are integrated so as to be opposite. The pair of slopes 10a are formed in a V-shape.

A molding face 11a having a rib and a groove corresponding to the ridge 6 and the valley 7 formed onto the upper face in the trunk portion 3 of the suturing needle A is formed onto the face of the upper mold 11 opposite the lower mold 10. The rib formed in the molding face 11a forms the valley 7 onto the upper face of the suturing needle A and is formed with a roundness corresponding to R3 set to the valley 7. The groove forms the ridge 6 onto the upper face of the suturing needle A and is formed with a roundness corresponding to R2 set to the ridge 6.

In this embodiment, the dimension in the direction along the pair of slopes 10a of the lower mold 10 and the upper mold 11 is substantially equal to the length except for the thread attaching portion 4 of a raw material 15 or has a value substantially equal to the length from the trunk portion 3 to the tapered portion 2 of the raw material 15.

When the lower mold 10 and the upper mold 11 are attached to a pressing machine, not illustrated, any one of the ribs of the molding face 11a formed on the upper mold 11 coincides with the center of the V-shape of the lower mold 10 and is set in this state.

The material having a circular section having a thickness corresponding to the thickness of the targeted suturing needle A is cut to the length corresponding to the length of the suturing needle A to form the raw material. First, the raw material is ground. Then, the straight needle-like raw material 15 formed with the portions corresponding to the needle tip portion 1, the needle tip 1a, the tapered portion 2, and the trunk portion 3 configuring the suturing needle A is formed.

The raw material 15 is placed on the slopes 10a of the lower mold 10 and is then pressed by the upper mold 11 to form an intermediate member 16 illustrated in FIG. 4. The pressed raw material 15 is molded along the slopes 10a of the lower mold 10 so as to have a substantially triangular section. The raw material 15 is not extended to the portion (the bottom portion of the V-shape) joined by the pair of slopes 10a of the lower mold 10 and has a deformed circumference so as to form the curved peak 5.

The raw material 15 is molded by the molding face 11a of the upper mold 11 along the longitudinal direction. The plural ridges 6 having the roundness R2 and the plural valleys 7 having the roundness R3 are molded with a predetermined pitch onto the upper face opposite the peak 5 of the portion corresponding to the trunk portion 3.

In the valley 7 formed in the substantially center of the upper face, the extension line of the vertical line of the valley 7 relative to the upper face crosses a portion of the peak 5, that is, any one of the curved portions configuring the peak 5. Thus, the valley 7 is located in the position opposite the peak 5.

As described above, a raw material 20 is pressed by the lower mold 10 and the upper mold 11. The intermediate member 16 illustrated in FIG. 4 can be formed. A hole for attaching the suturing thread is formed to the distal end face of the intermediate member 16. The intermediate material 16 is bent so that the peak 5 is arranged on the outer circumferential side and the upper face is arranged on the inner circumferential side. The suturing needle A illustrated in FIG. 1 can be configured.

Comparing Experiments

Figure 6:
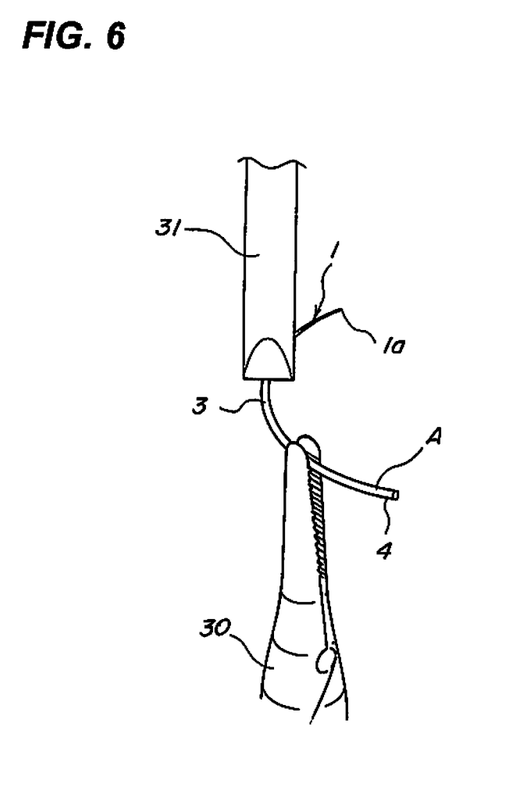
FIG. 6 is a diagram of assistance in explaining the state of conducting the holdability test of the suturing needle.

The comparing experiments of the holdability by the needle holder of the suturing needle A according to this embodiment and the related art suturing needles will be briefly described. FIG. 6 is a diagram of assistance in explaining the state of conducting the holdability test of the suturing needle.

As illustrated in FIG. 6, the trunk portion of the suturing needle A to be tested is held by the holding portion of a needle holder 30. The position separated from the portion held in this state by a constant distance is urged by a bar 31. The force applied to the bar 31 when the suturing needle cannot be reliably held by the needle holder due to the rotation of the suturing needle is measured for the holdability test.

The suturing needles to be tested have three different thicknesses (0.98 mm, 1.08 mm, and 1.28 mm). There are compared (i) the related art suturing needle having the trunk portion of circular section (flat-pressed circular body) having two planes made by pressing its two opposite faces, the planes being formed with the groove, (ii) the related art suturing needle which is formed with the groove onto the opposite face of the peak of the triangular section, is not formed so that the valley corresponds partially to the peak (the concave portion of the valley and the crest of the peak have a shift above 0.2 mm), and is not formed to have relations of R1≥R2≥R3 (misaligned triangular body), and the suturing needle A of the present invention having the three thicknesses.

In the flat-pressed circular body and the misaligned triangular body having a thickness of 0.98 mm, the reliability of the holding by the needle holder is deteriorated when the forces of about 32 N and about 34 N are applied. In the suturing needle A, the reliability of the holding by the needle holder is deteriorated when the force of about 40 N is applied. Therefore, the holdability is increased by about 17 to 25%.

In the flat-pressed circular body and the misaligned triangular body having a thickness of 1.08 mm, the reliability of the holding by the needle holder is deteriorated when the forces of about 40 N and 37 N are applied. In the suturing needle A, the reliability of the holding by the needle holder is deteriorated when the force of about 45 N is applied. Therefore, the holdability is increased by about 13 to 22%.

In the flat-pressed circular body and the misaligned triangular body having a thickness of 1.28 mm, the reliability of the holding by the needle holder is deteriorated when the forces of about 43 N and about 47 N are applied. In the suturing needle A, the reliability of the holding by the needle holder is deteriorated when the force of about 56 N is applied. Therefore, the holdability is increased by about 19 to 30%.

From the test results, the holdability of the suturing needle A according to this embodiment is found to be very good. This shows that the stronger acting force of the doctor via the needle holder can be reliably transmitted to the suturing needle A.

INDUSTRIAL APPLICABILITY

As described above, the suturing needle A according to the present invention can improve the holdability by the needle holder to efficiently transmit the force of the doctor and improve the operability. The suturing needle for any application can be used.

The invention claimed is:
1. A suturing needle comprising:
a needle tip portion having a needle tip for piercing tissue;
a tapered portion continuing to the needle tip portion;
a trunk portion continuing to the tapered portion; and
a thread attaching portion continuing to the trunk portion for connecting a suturing thread,
wherein the needle tip portion is formed to have a circular section continuing to a sharp needle tip, an angular section continuing to the sharp needle tip, a circular section continuing to a blunt needle tip or an angular section continuing to the blunt needle tip,
the tapered portion is formed to become gradually thicker from the needle tip portion to the trunk portion,
the trunk portion is formed to have a substantially triangular cross-section, an upper face of the trunk portion is formed of a wave shape having at least two ridges and slopes of the trunk portion are formed of two flat faces,
the trunk portion is also formed to have relations of R1≥R2≥R3, when a peak or a joint portion between the two flat faces, which is opposite to the upper face, has a radius of R1, a crest of the ridges has a roundness of R2, and a valley has a roundness of R3, the valley is formed to correspond partially to the peak, and the thickness becomes continuously larger from the tapered portion to the trunk portion.

2. The suturing needle according to claim 1, wherein the needle tip portion is formed to have a spherical shape with a diameter of from 0.2 to 0.6 mm.

3. The suturing needle according to claim 1, wherein the needle tip portion is formed to have a substantially triangular cross-section, and cutting edges are formed on two ridge lines of the substantially triangular cross-section.

4. The suturing needle according to claim 1, wherein the needle tip portion is formed to have a conical trapezoidal shape.

5. The suturing needle according to claim 1, wherein the suturing needle is curved and is formed so that the peak is arranged on an outer circumferential side of a curve, and the upper face is arranged on an inner circumferential side of the curve.

6. The suturing needle according to claim 1, wherein a concave portion of the valley and the crest of the peak are formed within the range of about 0.2 mm in the lateral direction in cross section.

7. A curved suturing needle comprising a needle tip portion having a needle tip for piercing tissue, a trunk portion continuing to the needle tip portion, and a distal end having a function of connecting a suturing thread and continuing to the trunk portion,
wherein the needle tip is round or flat blunt,
the trunk portion has a substantially triangular cross-section having a curved peak and a face opposite the peak,
the trunk portion has a peak arranged on an outer circumferential side of a curve and the face is arranged on an inner circumferential side of the curve,
the trunk portion is formed to have relations of $R1 \geq R2 \geq R3$, when the peak has a radius of $R1$, crests of ribs have roundness of $R2$, and a rounded groove has a roundness of $R3$,
and the trunk portion is formed so that at least two ribs are provided in a longitudinal direction of the suturing needle on a face opposite the curved peak to form the rounded groove between two adjacent ribs, and that one extension line of a vertical line of the rounded groove relative to a face crosses a portion of the peak.

8. The suturing needle according to claim 7, wherein the needle tip portion is formed to have a spherical shape with a diameter of from 0.2 to 0.6 mm.

9. The suturing needle according to claim 7, wherein the needle tip portion is formed with a substantially triangular cross-section and cutting edges are formed on two ridge lines on the substantially triangular cross-section.

10. The suturing needle according to claim 7, wherein a needle tip portion is formed with a conical trapezoidal shape.

11. The suturing needle according to claim 7, wherein a concave portion of a valley and a crest of the peak extend about 0.2 mm in the lateral direction in cross section.

* * * * *